United States Patent [19]

Kawakubo et al.

[11] Patent Number: 5,391,433
[45] Date of Patent: Feb. 21, 1995

[54] CARBON MATERIAL FOR ELECTRODES AND PROCESS FOR PREPARING IT

[75] Inventors: Takamasa Kawakubo, Tano; Yoshihisa Suda, Maebashi, both of Japan

[73] Assignee: Mitsubishi Pencil Kabushiki Kaisha, Tokyo, Japan

[21] Appl. No.: 971,283

[22] Filed: Nov. 4, 1992

[30] Foreign Application Priority Data

Nov. 29, 1991 [JP] Japan .................................. 3-339462

[51] Int. Cl.$^6$ ............................................ G01N 27/30
[52] U.S. Cl. .................................. 428/408; 204/294; 252/502; 313/348; 313/336; 313/341; 428/312.2; 428/318.6; 428/319.1; 445/46; 445/51
[58] Field of Search ................... 313/348, 336, 341; 445/46, 51; 252/502; 204/294; 428/408, 312.2, 318.6, 319.1

[56] References Cited

U.S. PATENT DOCUMENTS

| | | | |
|---|---|---|---|
| 4,034,031 | 7/1977 | Lersmacher et al. | 445/46 |
| 4,137,477 | 1/1979 | Krol et al. | 252/502 |
| 4,193,013 | 3/1980 | Futamoto et al. | 313/341 |
| 4,412,675 | 11/1983 | Kawakubo | 267/167 |
| 4,469,984 | 9/1984 | Sergeen et al. | 313/348 |
| 4,624,811 | 11/1986 | Waitkus et al. | 264/29.5 |

FOREIGN PATENT DOCUMENTS

| | | |
|---|---|---|
| 0121781 | 3/1984 | European Pat. Off. . |
| 2286107 | 9/1975 | France . |
| 3021427 | 1/1982 | Germany . |
| 56-156785 | 12/1981 | Japan . |
| 58-12201 | 7/1983 | Japan . |
| 1-250854 | 10/1989 | Japan . |
| 2-34902 | 8/1990 | Japan . |
| 3-85711 | 4/1991 | Japan . |
| 4-74958 | 2/1992 | Japan . |
| 4-74957 | 3/1992 | Japan . |

OTHER PUBLICATIONS

Database WPIL, Week 8436, Derwent Publications Ltd., London, GB:AN 84–222649 & JP-A-59 131 567 (Nippon Oil Seal Ind.) 28 Juillet 1984 *abstract*.
Patent Abstracts of Japan, vol. 11, No. 351 (E–557) 17 Nov. 1987 & JP-A-62 128 452 (Meidensha Electric MGF Co.) 10 Jun. 1987 *abstract*.
Patent Abstracts of Japan, vol. 8, No. 200 (E–266) 13 Sep. 1984 & JP-A-59 087 777 (Matsushita Denki Sangyo KK) 21 May, 1984 *abstract*.
Patent Abstracts of Japan, vol. 15, No. 052 (C–0803) 7 Feb., 1991 & JP-A-22 83 667 (Ibiden Co., Ltd.) 21 Nov. 1990 *abstract*.
Ser. No. 325,291 Filed on Mar. 17, 1989 for Hiroko Kaneko et al.
Ser. No. 905,768 Filed on Jun. 29, 1992 for Akira Negisi et al.

(List continued on next page.)

Primary Examiner—A. A. Turner
Attorney, Agent, or Firm—Darby & Darby

[57] ABSTRACT

A carbon material for electrodes which is a graphite/glass like carbon composite material having a structure in which the crystals of the graphite are oriented in one direction in the matrix of the glass like carbon so as to possess an electrode reaction activity inherent in the graphite crystals, having a maximum pore diameter of 150 Å or less, and having electrolyte non-penetrative properties substantially corresponding to those of the glass like carbon; and a process for preparing a carbon material for electrodes which comprises the steps of highly dispersing, composing and orienting a graphite fine powder of the sufficiently grown crystals in an organic substance which can leave a glass like and less graphitizable carbon when calcined in a non-oxidizing atmosphere, and then calcining and carbonizing the composition. The carbon material of the present invention permits applying both current and voltage to biological systems, has no toxicity, such mechanical strength as to permit detecting a trace portion and reproducibility, can measure an electrode reaction stably, and is inexpensive.

2 Claims, 2 Drawing Sheets

OTHER PUBLICATIONS

Ser. No. 905,767 Filed on Jun. 29, 1992 for Hiroko Kaneko et al.

Hiro Kaneko et al., *Extended Abstracts* 2, 21-11-18 -P, d1, "Electrochemical Behavior of GRC electrodes for Voltammetry".

T. Abe, et al., *Extended Abstracts* 2, 21-13-04-P, d1, "Fabrication and Application of Non-Carbon Microelectrodes to *In-Vivo* Voltammetry".

Hiroko Kaneko, et al., *Extended Abstracts* 2, 18-14-1-0-P, d5, "Rodox Reactions of Vanadium Ions on GRC and Carbon Fiber Electrodes".

The Japan Association for the Advancement of Science, The 17th Committee Materials 117-213-c-1, Feb. 1, 1991.

Takamasa Kawakubo et al., "Electrochemical Behavior of Carbon Microelectrodes Prepared by Using Graphite/Carbon Composite", *Tanso 152*:106-114, (1992).

CARBON MATERIAL FOR ELECTRODES AND PROCESS FOR PREPARING IT

BACKGROUND OF THE INVENTION (i) Field of the Invention

The present invention relates to a carbon material for electrodes which are used in electrochemical detectors, sensors for environmental analysis, sensors for pathologic inspection, and probe electrodes for detection which are required to be harmless and nonpoisonous to biological systems and foods, and it also relates to a process for preparing the carbon material.

(ii) Description of the Prior Art

In a wide field of electrochemical measuring techniques, an abbreviated rapid analysis which has been swiftly developed in recent years and which utilizes a sensor as a detecting means permits performing a measurement with very high selectivity and high sensitivity. Therefore, the use of the abbreviated rapid analysis is begun to analyze and evaluate biological samples and environmental samples containing trace amounts of many compounds which are components to be measured.

Furthermore, nowadays, it has been very important to obtain, for example, biological information of such specific substances on a cellular level in vivo in situ in local parts of the biological system and the like by the use of a sensor electrode capable of detecting them with high sensitivity. For this purpose, the electrode is used as follows: The electrode is disposed or stuck in the vicinity of an aimed cell of an organism to give physical, chemical and electrical stimulation to the cell, so that a response substance is released or a chemical change occurs, with the result that a specific substance is produced. At this time, the electrode is required to select and measure the thus produced specific substance.

A selected electrode material for a working electrode of the electrochemical detector has a large influence on a kind of substance to be measured and the possibility of quantitative analysis. Heretofore, as such a working electrode for voltammetry, there have been investigated a mercury dropping electrode, a static mercury electrode, platinum, gold, gold amalgam, copper and various conformations of carbon (glass like carbon, carbon fiber, carbon paste and pyrolitic graphite), but the mercury electrode and the glass like carbon are predominantly used as an electrode for polarographies and as an electrode for electrochemical detectors, respectively.

However, the polarography has a problem of safety, since it uses toxic mercury. The glass like carbon also has many drawbacks which should be eliminated. That is, the glass like carbon has low current sensitivity, and when a high positive potential is applied thereto through an electrolyte, the reproducibility on the surface of the electrode deteriorates. Thus, a utilizable potential range is limited to about +1.0 V or less. In addition, the glass like carbon is largely affected by a pretreatment such as an oxidizing treatment, and so the reproducibility of the measurement is unreliable.

The platinum electrode cannot be used on the negative side of a hydrogen generating potential, and additionally its pretreatment is also difficult.

The gold electrode is less resistant to halide ions. Since these electrodes are made of the metals, they are dissolved when used, thereby releasing toxic ions which harm the biological system. However, there are not good electrodes which can take the place of them, and hence these electrodes have been still unavoidably used. Moreover, in these days, a carbon micro-electrode comprising one carbon fiber (having a diameter of several micrometers) has been begun to be on the market, but according to a pursuit test by the present inventors, it has been apparent that the carbon micro-electrode has the large variation of electrochemical properties, poor reproducibility of data, and very low reliability.

Graphite has a wide polarized potential domain, an electrode reaction activity and a less toxicity to the organisms, and therefore it is a useful material. However, the graphite is poor in mechanical strength, and when it is used singly, an electrolyte penetrates into its structure. For the prevention of this penetration, the graphite is required to be impregnated with an oil or resin. Nevertheless, in the system in which even a small amount of an organic solvent is contained, the material with which the graphite has been impregnated is dissolved therein, and the variation of the electrochemical properties increases, so that the reproducibility of data is poor.

SUMMARY OF THE INVENTION

The present invention intends to remove the drawbacks of the above-mentioned conventional electrode materials.

A first object of the present invention is to provide a carbon material for electrodes by which both current and voltage can be applied to biological systems and which has no toxicity (which is safe, even if it remains in the biological systems) and which can be used to inspect foods, and to provide a process for preparing the same.

A second object of the present invention is to provide a carbon material for electrodes which permits electrochemically detecting an extremely slight (trace) portion and which has mechanical strength, and to provide a process for preparing the same.

A third object of the present invention is to provide an inexpensive carbon material for electrodes which has the less variation of electrode properties and the reproducibility of data and which can stably measure an electrode reaction without requiring any specific pretreatment.

That is, the aspects of the present invention are as follows.

(1) A carbon material for electrodes which is a graphite/glass like carbon composite material having a structure in which the crystals of the graphite are oriented in one direction in the matrix of the glass like carbon so as to possess an electrode reaction activity inherent in the graphite crystals, having a maximum pore diameter of 150 Å or less, and having electrolyte non-penetrative properties substantially corresponding to those of the glass like carbon.

(2) The carbon material for electrodes described in the preceding paragraph (1) wherein 65 to 95% of the graphite/glass like carbon composite material is constituted of the matrix of the non-penetrative glass like carbon.

(3) A process for preparing a carbon material for electrodes which comprises the steps of highly dispersing and composing a graphite fine powder of the sufficiently grown crystals in an organic substance which can leave a glass like and less graphitizable carbon when calcined in an inert atmosphere or a non-oxidizing atmosphere, extruding the composition into a desired form, so that orienting, in an extrusion direction, graphite crystals of the composition, and then calcining the composition up to a high temperature in the inert atmosphere or the non-oxidizing atmosphere to carbonize the contained organic substance.

(4) The process for preparing a carbon material for electrodes described in the preceding paragraph (3) wherein the organic substance which can leave the glass like and less graphitizable carbon is at least one selected from the group consisting of an organic polymeric material, its monomer or oligomer, a tar, a pitch, a carbonized pitch, a thermoplastic resin and a prepolymer of a thermosetting resin.

(5) The process for preparing a carbon material for electrodes described in the preceding paragraph (4) wherein the organic polymeric substance is one selected from the group consisting of lignin, cellulose, tragacanth gum, gum arabi, natural gum and its derivative, a compound having a condensed polycyclic aromatic moiety in the basic structure of the molecule, dinitronaphthalene, pyrene, pyranthrone, violanthrone, an indanthrene-based vat dye derived from benzanthrone, and its intermediate.

(6) The process for preparing a carbon material for electrodes described in the preceding paragraph (4) wherein the thermoplastic resin is a resin obtained by oxidizing and crosslinking, as a carbon precursor-producing treatment, one selected from the group consisting of polyvinyl chloride, polyacrylonitrile, polyvinylidene chloride, chlorinated polyvinyl chloride, polyvinyl acetate, polyvinyl alcohol, polyvinyl pyrrolidone, ethyl cellulose, carboxymethyl cellulose, polyvinyl chloride.vinyl acetate copolymer, polyphenylene oxide, polyparaxylene, polysulfone, polyimide, polyamideimide, polybenzimidazole and polyoxadiazole.

(7) The process for preparing a carbon material for electrodes described in the preceding paragraph (4) wherein the thermosetting resin is at least one prepolymer selected from the group consisting of a phenolic resin, a furan resin, an epoxy resin, a xylene resin and a COPNA resin, and when heated, the thermosetting resin can flow, produce an intermolecular crosslinkage, and then cure in a three-dimensional form, and it can give a high carbon residue yield without any specific carbon precursor-producing treatment.

(8) The process for preparing a carbon material for electrodes described in the preceding paragraph (4) wherein the pitch is what is obtained by subjecting a petroleum pitch, a coal tar pitch, an asphalt, or a carbonized pitch of the pitch or a hydrocarbon compound comprising a synthetic resin to an anti-graphitization treatment comprising an oxidizing treatment for the purpose of crosslinking it.

(9) The process for preparing a carbon material for electrodes described in the preceding paragraph (3) wherein a mesophase pitch having a carbon residue yield of 75-95% formed by carbonizing a pitch to increase a carbon residue, and then crosslinking the same to obtain anti-graphitization properties is mixed with an organic substance which constitutes a matrix and which becomes a glass like carbon, and the mixture is then co-carbonized.

(10) The process for preparing a carbon material for electrodes described in the preceding paragraph (3) wherein the graphite fine powder is one selected from the group consisting of graphite whisker, highly oriented pyrolitic graphite (HOPG), Kish graphite, natural graphite and artificial graphite.

(11) The process for preparing a carbon material for electrodes described in the preceding paragraph (3) wherein the calcination and the carbonization are carried out by a heat treatment at a temperature of 500° to 2500° C. in an inert atmosphere or a non-oxidizing atmosphere.

DETAILED DESCRIPTION OF THE INVENTION

Figure 1:
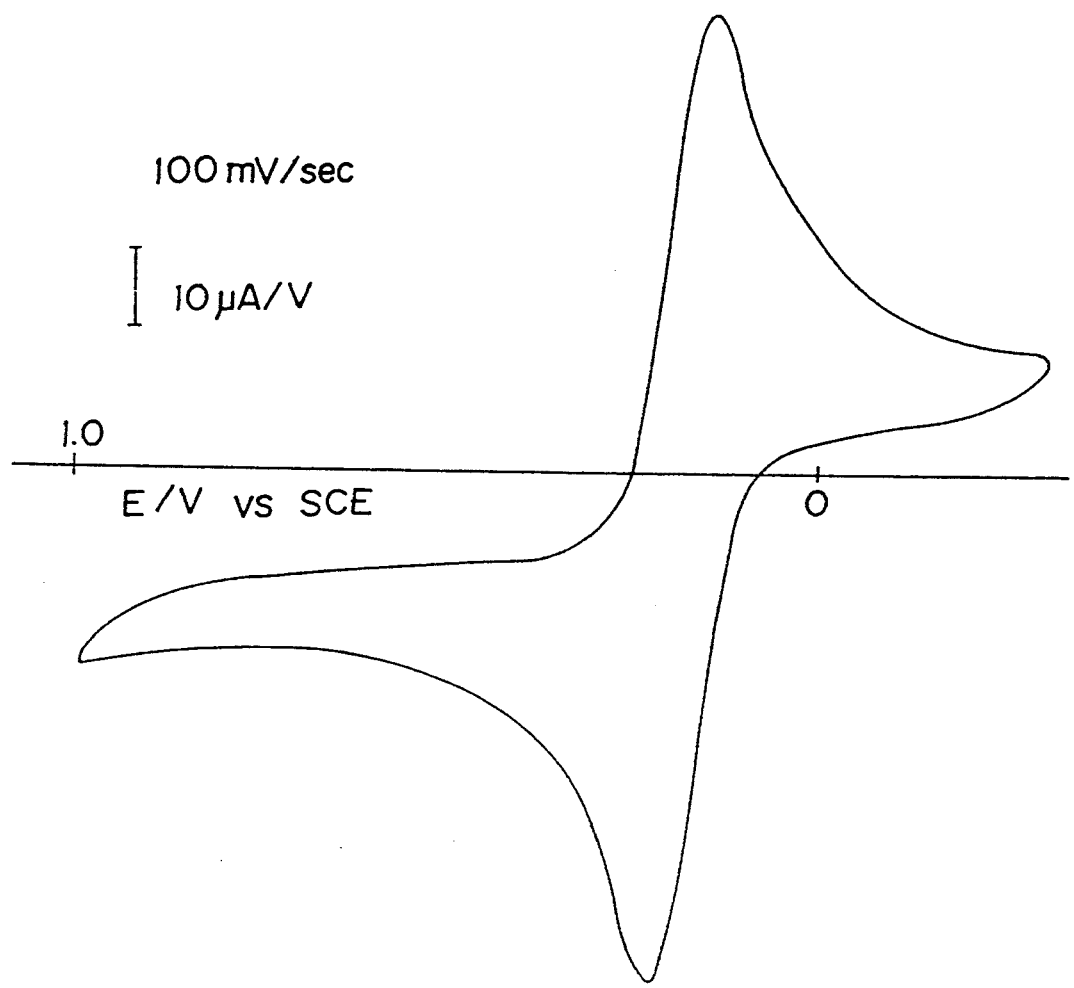
FIG. 1 shows a redox reactivity of ferrocyanate ions/ferricyanate ions in the 1M KCl system of $5 \times 10^{-3}$ M $Fe(CN)_6^{4-}$ in accordance with cyclic voltammetry by the use of a carbon material electrode of the present invention.

The present inventors have paid much attention to a fact that the crystal edge surface of graphite has extremely excellent properties which are not present in other materials, that is, it is rich in an electrode reactivity, has a large polarized potential domain, can be easily pretreated, does not deteriorate with time, has high stability, does not dissolve, and is free from toxicity. Thus, the present inventors have intensively researched, and as a result, they have found that an electrode material comprising a novel graphite/glass like carbon composite carbon having non-permeability by itself without requiring impregnation with an oil or a resin and large mechanical strength which can be obtained by using a glass like carbon showing non-permeability as a matrix and orientating graphite in one direction. On the basis of this knowledge, the present invention has been completed.

In the carbon material for electrodes which is the graphite/glass like carbon composite carbon of the present invention, 65-95% of the constitutional material comprises a glass like carbon matrix having non-permeability formed by using, as a starting material, an organic resin material having a three-dimensional crosslinkage or a natural organic material which can be carbonized in a solid phase. In the case that it is required to further heighten density, a mesophase pitch having a carbon residue yield of 75-95% formed by carbonizing a pitch to increase a carbon residue content and to obtain anti-graphitization properties is blended with the glass like carbon matrix and then co-carbonized. When the content of the matrix carbon is less than 65%, defects and pores are generated in the material and the inherent non-permeability is lost unpreferably. Furthermore, when the content of the matrix carbon is more than 95%, the active electrode reaction properties which the graphite crystals have are lost unpreferably.

An organic substance which constitutes the matrix material and which can leave a glass like and less graphitizable carbon when calcined in an inert atmosphere or a non-oxidizing atmosphere is an organic resin material having a three-dimensional crosslinkage or a natural organic material which can be carbonized in a solid phase. Typical examples of the organic substance include an organic polymeric substance and one or a mixture of two or more of a monomer and an oligomer of the organic polymeric substance, a tar, a pitch, a carbonized pitch, a thermoplastic resin and a prepolymer of a thermosetting resin.

Here, the organic polymeric substance is a substance other than the undermentioned thermoplastic resin and thermosetting resin, and examples of the organic polymeric substance include lignin, cellulose, tragacanth gum, gum arabi, natural gum and its derivative, a compound having a condensed polycyclic aromatic moiety such as saccharide, chitin or chitosan in the basic structure of the molecule, formalin condensate of naphthalenesulfonic acid, dinitronaphthalene, pyrene, pyranthrone, violanthrone, an indanthrene-based vat dye derived from benzanthrone, and its intermediate.

The thermoplastic resin is a resin obtained by oxidizing and crosslinking, as a carbon precursor-producing treatment, a usual thermoplastic resin such as polyvinyl chloride, polyacrylonitrile, polyvinylidene chloride, chlorinated polyvinyl chloride, polyvinyl acetate, polyvinyl alcohol, polyvinyl pyrrolidone, ethyl cellulose, carboxymethyl cellulose, polyvinyl chloride.vinyl acetate copolymer, or a heat-resistant thermoplastic resin such as polyphenylene oxide, polyparaxylene, polysulfone, polyimide, polyamide-imide, polybenzimidazole and polyoxadiazole.

The thermosetting resin is a phenolic resin, a furan resin, an epoxy resin, a xylene resin and a COPNA resin, and when heated, the thermosetting resin can flow, produce an intermolecular crosslinkage, and then cure in a three-dimensional form, and it can give a high carbon residue yield without any specific carbon precursor-producing treatment.

The pitch is what is obtained by subjecting a petroleum pitch, a coal tar pitch, an asphalt, or a carbonized pitch (which is treated at 400° C. or less and which has a carbon residue yield of 75-95%) of a hydrocarbon compound such as a pitch or a synthetic resin being carried out an anti-graphitization treatment such as an oxidizing treatment for the purpose of crosslinking it.

Next, reference will be made to a graphite fine powder to be used in a composite form with the organic material which is the starting material of the matrix carbon. In order to achieve the good electrode reaction, it is important to prepare a composite carbon material which is systematically oriented so that the crystal edge surface of the highly developed graphite may be arranged vertically to the reaction surface of the electrode. Therefore, graphite whisker, highly oriented pyroiltic graphite (HOPG), Kish graphite, crystalline natural graphite can be used preferably. The particle diameter of the graphite fine powder is preferably several micrometers or less in terms of a maximum diameter, depending upon the diameter of the desired electrode.

Next, the preparation process of the present invention will be described. As starting material, the one or more organic substances which can leave the glass like and less graphitizable carbon constituting the matrix are selected from the above-mentioned natural polymeric substance, synthetic polymeric substance, thermosetting resin, thermoplastic resin and pitches, and the one or more selected organic substances are then blended with the above-mentioned crystalline carbon fine powder in compliance with a purpose and the fine powder is sufficiently dispersed therein by a Henschel mixer or the like.

If it is necessary to heighten density or to smooth the surface of the system, a carbonized pitch having a high carbon residue yield is blended with the above-mentioned composition, and a plasticizer, a solvent and the like are then added thereto. Afterward, they are sufficiently mixed/dispersed by a kneader such as a pressure kneader or a twin roll by which shearing force can be highly given. After granulated by a pelletizer, the resultant granules are extruded at a high velocity so as to have a desired diameter by means of a screw type or a plunger type extruder, and an orientating operation is then carried out so as to successfully arrange the crystals of the mixed graphite in an extrusion direction, whereby a molded article is obtained.

Next, this molded article is treated for 10 hours in an air oven heated to 180° C., while stretched, to form a carbon precursor material. Furthermore, it is gradually heated up to 1500° C. in a nitrogen gas, while a temperature rise velocity is controlled, to complete the carbonization, thereby obtaining a carbon material for electrodes.

Depending upon the purpose, the carbon material may be densified all over by carrying out a heat treatment up to 2200° C. in vacuo or in an argon gaseous phase.

By using the above-mentioned carbon material for electrodes of the present invention, there can be prepared a novel carbon electrode for electrochemical measurement which has a non-permeability corresponding to that of a glass like carbon and an electrode reaction activity on the edge surfaces of graphite crystals. The carbon electrode prepared from the carbon material for electrodes of the present invention can be easily reused by breaking off a used portion thereof to expose a new section of the electrode, since it does not require any special pretreatment. Additionally, in the carbon material for electrodes of the present invention, the deterioration of the electrode reaction activity can be sufficiently inhibited, in contrast to the glass like carbon.

EXAMPLES

Example 1

A mixed resin system of 35% by weight of a chlorinated vinyl chloride resin (T-742, made by Nippon Carbide Industries Co., Ltd.) and 50% by weight of a furan resin (Hitafuran VF-302, made by Hitachi Chemical Co., Ltd.) was used as a matrix carbon material of an electrode, and 15% by weight of a natural graphite fine powder (average particle diameter=1 μm, CSSP-B, made by Nippon Graphite Co., Ltd.) was added to the mixed resin system to form a composition. Next, 20% by weight of diallyl phthalate monomer was added as a plasticizer to 100% by weight of the resultant composition and then dispersed therein by the use of a Henschel mixer. Afterward, the mixture was sufficiently repeatedly kneaded by the use of a twin roll for mixing whose surface temperature was maintained at 120° C., thereby obtaining a sheet-like composition. This composition was further pelletized by a pelletizer to obtain a composition for molding in the form of pellets. These pellets were extruded at 130° C. at a velocity of 3 m/second by a screw type extruder with a die having a diameter of 0.7 mm, while deaerated, and the molded article was fixed on a frame and then treated for 10 hours in an air oven heated up to 180° C. to form a carbon precursor wire material. Next, this wire material was heated up to 500° C. at a temperature rise rate of 10° C./hour and then up to 1000° C. at a temperature rise rate of 50° C./hour, and afterward, it was further heated up to 1500° C. at 100° C./hour, maintained at 1500° C. for 3 hours, and then allowed to stand, whereby the calcination was completed.

In the thus obtained carbon material for electrodes, a graphite/matrix carbon ratio was 32/68. The pore diameter of the system was measured in accordance with a mercury pressure method by the use of a porosimeter (Autoscan-60) made by Yuasa Ionics Co., Ltd., and as a result, the maximum pore diameter was 120 Å. Electrode properties were evaluated by observing the redox reactivity of ferrocyanate ions/ferricyanate ions in the 1M KCl system of $5 \times 10^{-3}$ M $Fe(CN)_6^{4-}$ as the standard of an electrode reaction activity by the use of a polarographic analyzer (YANACO P-1100) made by Yanagimoto Co., Ltd., and the results are shown FIG. 1. Even when any special pretreatment was not made, blank current was small, and sharp peaks of a oxidation wave and a reduction wave were obtained and a difference $\Delta Ep$ between peak potentials was near to a theoretical value. In addition, the increase of a current value attributed to the permeation of the electrolyte was not observed, which meant that the carbon material had non-permeability against the electrolyte substantially corresponding to a glass like carbon.

Example 2

A mixed resin system of 50% by weight of a furan resin (Hitafuran VF-302, made by Hitachi Chemical Co., Ltd.) and 30% by weight of a carbonized pitch (carbon residue yield =85%, MH-1P, made by Kureha Chemical Industry Co., Ltd.) was used as a matrix carbon material of an electrode, and 20% by weight of a natural graphite fine powder (average particle diameter=1 μm, CSSP-B, made by Nippon Graphite Co., Ltd.) was added to the mixed resin system and then dispersed therein by the use of a Henshel mixer. Afterward, the mixture was sufficiently repeatedly kneaded by the use of a twin roll for mixing whose surface temperature was maintained at 120° C., thereby obtaining a sheet-like composition. This composition was vacuum-extruded at a discharge rate of 5 m/second by the use of a plunger type oil hydraulic extruder. Afterward, the same procedure as in Example 1 was carried out to obtain a desired carbon material for electrodes.

In the thus obtained carbon material for electrodes, a graphite/matrix carbon ratio was 30/70. The maximum pore diameter of the system was 65 Å.

Figure 2:
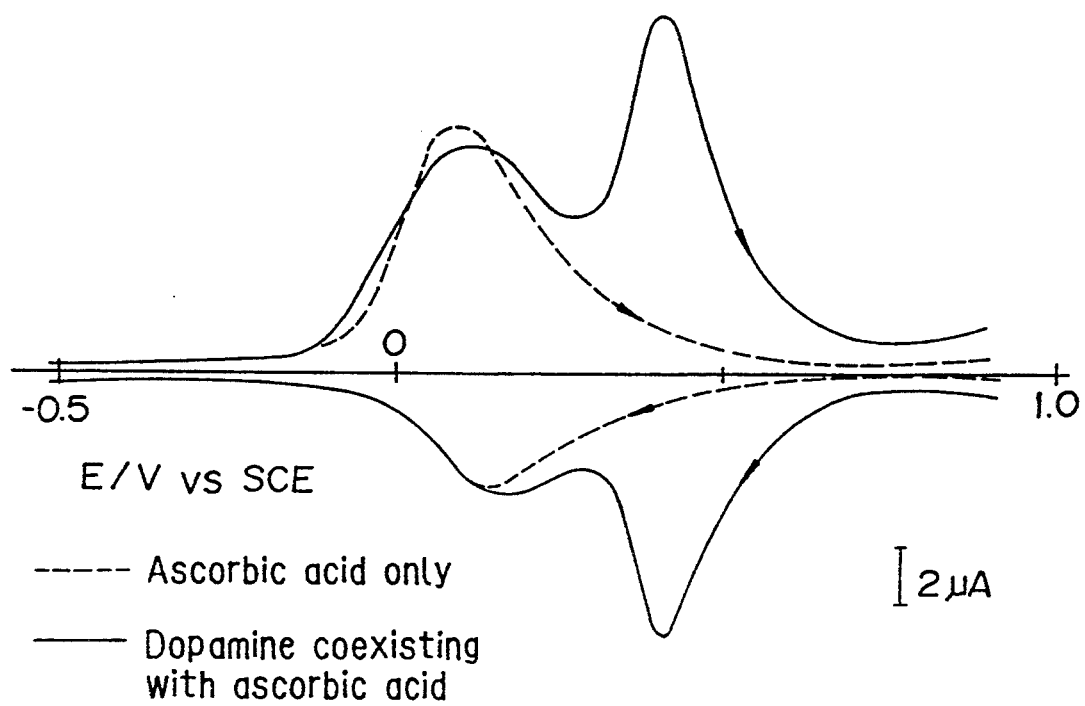
FIG. 2 shows measured results of dopamine in the presence of ascorbic acid in a Ringer's solution by the use of a carbon material electrode of the present invention.

In reference to the electrode characteristic, a measured result by differntial pulse voltammetry method regarding dopamine coexisting together ascorbic acid in Ringer's solution is shown in FIG. 2.

A current peak at 0.15 V vs. Standard Caromel Electrode (S.C.E.) was observed when only ascorbic acid was present.

50 μM concentration of dopamine was separately observed in coexistence of 500 μM concentration of ascorbic acid. That is, the respective corresponding peaks at 0.15 V and 0.4 V vs. S.C.E. were observed with good reproducibility in the coexisting state of ascorbic acid and dopamine. The fact shows that the electrode is extremely active in comparison with being unable to separately detect the respective oxydation-reduction waves by overlapping each other in the case of almost carbon electrodes. In addition, the increase of a current value attributed to the permeation of the electrolyte was not observed, which meant that the carbon material had non-permeability against the electrolyte substantially corresponding to a glass like carbon.

What is claimed is:

1. A carbon material for electrodes which is a graphite/glass like carbon composite material having a structure in which the crystals of the graphite are oriented in one direction in the matrix of the glass like carbon so as to possess an electrode reaction activity inherent in the graphite crystals, having a maximum pore diameter of 150 Å or less, and having electrolyte non-penetrative properties substantially corresponding to those of the glass like carbon.

2. A carbon material for electrodes which is a graphite/glass like carbon composite material having a structure in which the crystals of the graphite are oriented in one direction in the matrix of the glass like carbon so as to possess an electrode reaction activity inherent in the graphite crystals, having a maximum pore diameter of 150 Å or less, and having electrolyte non-penetrative properties substantially corresponding to those of the glass like carbon, wherein 65 to 95% of the graphite/glass like carbon composite material is constituted of the matrix of the non-penetrative glass like carbon.

* * * * *